Figure 1:
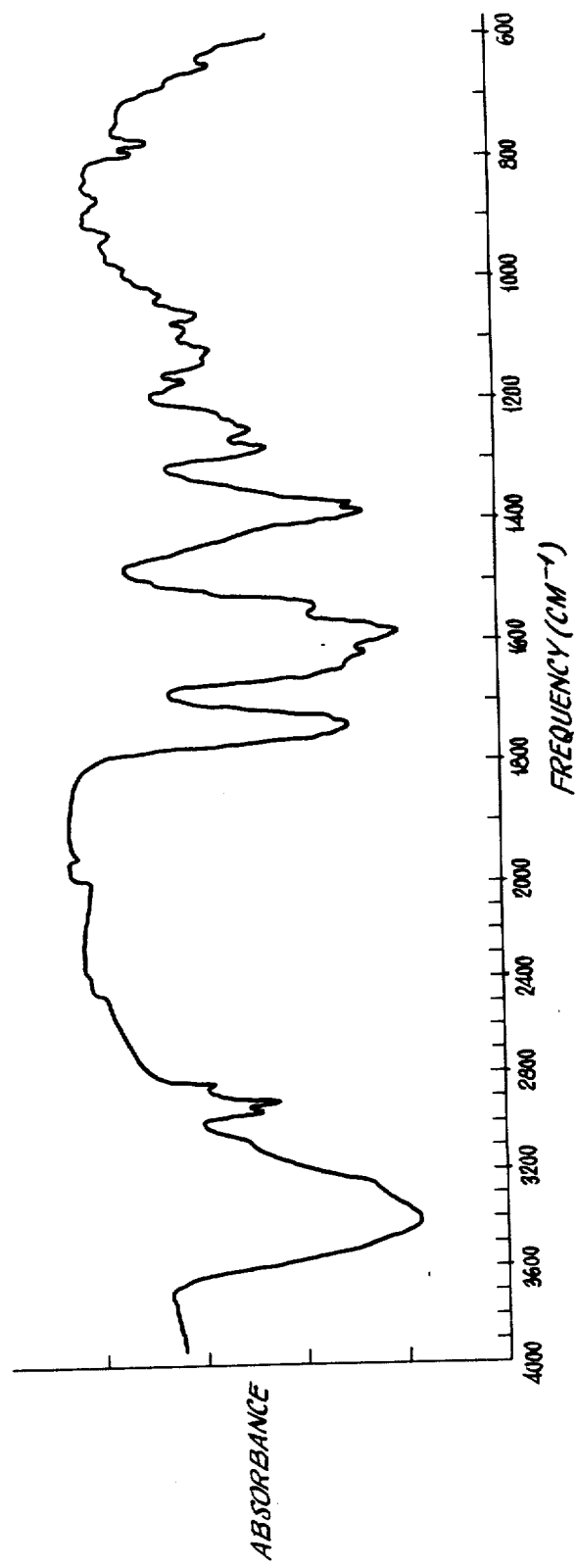

United States Patent [19]

Kahan et al.

[11] 4,165,379
[45] Aug. 21, 1979

[54] N-ACETYL THIENAMYCIN

[75] Inventors: Jean S. Kahan; Frederick M. Kahan, both of Rahway; Robert T. Goegelman, Linden; Edward O. Stapley, Metuchen, all of N.J.; Sebastian Hernandez, Madrid, Spain

[73] Assignee: Merck & Co., Inc., Rahway, N.J.

[21] Appl. No.: 827,503

[22] Filed: Aug. 25, 1977

Related U.S. Application Data

[63] Continuation of Ser. No. 634,301, Nov. 21, 1975, abandoned.

[51] Int. Cl.$^2$ .................. C07D 487/04; A61K 31/40
[52] U.S. Cl. ........................ 424/274; 260/326.31; 435/119; 435/886
[58] Field of Search .................... 260/326.31; 424/274

[56] References Cited

U.S. PATENT DOCUMENTS

| 3,950,357 | 4/1976 | Kahan et al. ............ 260/326.31 |
| 4,000,161 | 12/1976 | Geogelman et al. ....... 260/326.31 |

FOREIGN PATENT DOCUMENTS 839324  3/1975  Belgium ........................ 424/274

Primary Examiner—Donald G. Daus
Assistant Examiner—Mary Lee
Attorney, Agent, or Firm—Hesna J. Pfeiffer; James A. Arno; Julian S. Levitt

[57] ABSTRACT

The antibiotic N-acetyl thienamycin and its non-toxic pharmaceutically acceptable salts are active against both gram-positive and gram-negative bacteria. The antibictic is produced by growing a species of Streptomyces on suitable fermentation media or alternatively by acetylation of thienamycin.

2 Claims, 1 Drawing Figure

N-ACETYL THIENAMYCIN

N-ACETYL THIENAMYCIN

This is a continuation of application Ser. No. 634,301, filed Nov. 21, 1975, now abandoned.

BACKGROUND OF THE INVENTION

The discovery of the remarkable antibiotic properties of penicillin stimulated great interest in this field which has resulted in the finding of many other valuable antibiotic substances such as other penicillins, cephalosporins, streptomycin, bacitracin, tetracyclines, chloramphenicol, erythromycins and the like. In general, the antibacterial activity of each of these antibiotics does not include certain clinically important pathogenic bacteria. For example, some are principally active against only gram-positive types of bacteria. Furthermore, acquired resistance over the course of widespread use of existing antibiotics in the treatment of bacterial infection has caused a serious resistance problem to arise.

Accordingly, the deficiencies of the known antibiotics have stimulated further research to find other antibiotics which will be active against a wider range of pathogens as well as resistant strains of particular microorganisms.

SUMMARY OF THE INVENTION

This invention relates to a new antibiotic agent. More particularly, it is concerned with a new antibiotic substance, herein called N-acetyl thienamycin. The invention encompasses the antibiotic in dilute forms, as crude concentrates and in pure forms.

It is an object of the present invention to provide a new and useful antibiotic which is highly effective in inhibiting the growth of various gram-negative and gram-positive microorganisms. Another object is to provide a process for the preparation of this novel antibiotic substance by the fermentation of nutrient media with a microorganism or alternatively by acetylation of thienamycin. Other objects will be apparent from the detailed description of this invention hereinafter provided.

The novel antibiotic substance of the present invention, N-acetyl thienamycin, is produced by growing under controlled conditions the microorganism *Streptomyces cattleya*. Growth of *Streptomyces cattleya* in a nutrient media also results in the production of thienamycin. Acetylation of thienamycin provides a further process for the preparation of N-acetyl thienamycin. The preparation of thienamycin by fermentation of *Streptomyces cattleya* is set forth herein and also in the co-pending U.S. applications Kahan, et al. Ser. No. 526,992, filed Nov. 25, 1974 and Goegelman et al., Ser. No. 613,822 filed Sept. 18, 1975 which is a continuation-in-part application of Goegelman et al., Ser. No. 534,382 filed Dec. 19, 1974, now abandoned which are herein incorporated by reference.

Based upon extensive taxonomic studies, *Streptomyces cattleya*, isolated from a soil sample, was identified as an actinomycete and has been designated MA-4297 in the culture collection of MERCK & CO., Inc. Rahway, N.J. A culture thereof has been placed on permanent deposit with the culture collection of the Northern Regional Research Laboratories, Northern Utilization Research and Development Division, Agricultural Research Service, U.S. Department of Agriculture, Peoria, Ill., and has been assigned accession No. NRRL 8057.

The morphological and cultural characteristics of *Streptomyces cattleya* are set forth in Table 1.

TABLE 1

Morphology

Sporophores are compact spirals occurring as side and terminal branches as aerial mycelium. Spores are ellipsoidal to cylindrical in shape, $0.9\mu \times 1.2\mu$ in size, occurring in chains of more than 10.

Cultural

Tomato paste-oatmeal agar
  Vegetative growth—Reverse-tan, flat, spreading;
  Aerial mycelium—Orchid (10 gc) mixed with white;
  Soluble pigment—None.
Czapek Dox agar (sucrose nitrate agar)
  Vegetative growth—Colorless, flat, spreading;
  Aerial mycelium—Sparse, pinkish white;
  Soluble pigment—None.
Egg albumin agar
  Vegetative growth—Tan with grayed-orchid cast, flat, spreading;
  Aerial mycelium—Orchid (10 gc) mixed with lighter shades of orchid and some white;
  Soluble pigment—None.
Glycerol asparagine agar
  Vegetative growth—Reverse-tan with gray-pink cast, flat, spreading;
  Aerial mycelium—Orchid (10 gc) mixed with some white;
  Soluble pigment—None.
Yeast extract-glucose + salts agar
  Vegetative growth—Tan with grayed pink cast;
  Aerial mycelium—Orchid (10 gc) mixed with pinkish-white;
  Soluble pigment—None.
Yeast extract-malt extract agar
  Vegetative growth—Tan;
  Aerial mycelium—Orchid (10 gc) mixed with pinkish-white;
  Soluble pigment—None.
Peptone-iron-yeast extract agar
  Vegetative growth—Tan;
  Aerial mycelium—None;
  Soluble pigment—Slight browning of medium;
  Melanin—Negative;
  $H_2S$ production—Negative.
Nutrient agar
  Vegetative growth—Light tan;
  Aerial mycleium—None;
  Soluble pigment—None.
Nutrient starch agar
  Vegetative growth—Cream to tan;
  Aerial mycelium—None;
  Soluble pigment—None;
  Hydrolysis of starch—Moderate.
Nutrient gelatin agar
  Vegetative growth—Cream-colored;
  Aerial mycelium—None;
  Soluble pigment—None;
  Liquefaction of gelatin—Moderate.
Gelatin stabs
  Vegetative growth—Tan;
  Aerial mycelium—None;
  Soluble pigment—None;
  Liquefaction of gelatin—Moderate.
Potato plug
  Vegetative growth—Moderate, tan;
  Aerial mycelium—Sparse, grayish-pinkish-white;

Soluble pigment—None.
Loeffler's Blood serum
 Vegetative growth—Cream-colored;
 Aerial mycelium—None;
 Soluble pigment—None;
 Liquefaction—None.
Skim milk agar
 Vegetative growth—Tan;
 Aerial mycelium—Sparse, whitish;
 Soluble pigment—Slight browning of medium;
 Hydrolysis of casein—Positive.
Litmus milk
 Vegetative growth—Tan to brown;
 Aerial mycelium—None;
 Color—No soluble pigment, litmus indicator becoming bluish;
 Coagulation and/or peptonization—Partial peptonization, becoming alkaline.
Skim milk
 Vegetative growth—Tan;
 Aerial mycelium—None;
 Soluble pigment—None;
 Coagulation and/or peptonization—Partial peptonization, becoming alkaline.
Tyrosine agar
 Vegetative growth—Tan;
 Aerial mycelium—Mixture of orchid (10 gc) and white;
 Soluble pigment—None;
 Decomposition of tyrosine—Positive.

All of the readings reported above were taken after three weeks incubation at 28° C. unless noted otherwise. The pH of the media used in these studies was approximately neutral, namely, pH 6.8-7.2. The color designations used in the description are in accordance with the definitions of the *Color Harmony Manual*, 4th Edition (1958), Container Corporation of America, Chicago, Ill.

*Streptomyces cattleya* was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8-7.2). Table 2 shows the utilization of these carbohydrate sources by *Streptomyces cattleya*: + indicating good growth, ± poor growth, and − no growth on the particular carbohydrate.

TABLE 2

| Glucose | + | Maltose | ± |
|---------|---|---------|---|
| Arabinose | − | Mannitol | + |
| Cellulose | − | Mannose | ± |
| Fructose | ± | Raffinose | − |
| Inositol | − | Rhamnose | − |
| Lactose | − | Sucrose | ± |
| Xylose | ± | | |

The amount of growth with change in temperature, the oxygen requirement and the effect on nitrate by the microorganism is as follows:
Temperature range (Yeast extract-glucose+salts agar);
 28° C.—Good
 37° C.—Moderate
 50° C.—No growth
Oxygen requirement (Stab culture in yeast extract-glucose+salts agar);
 Aerobic
Nitrate reduction—Positive.

It is to be understood that for the production of the new antibiotic of this invention, the present invention is not limited to the organism *Streptomyces cattleya* or to organisms fully answering the above growth and microscopic characteristics which are given for illustrative purposes. In fact, it is desired and intended to include the use of mutants produced from the described organism by various means, such as X-radiation, ultra-violet radiation, nitrogen mustard, phage exposure and the like.

The novel antibiotic of the invention, N-acetyl thienamycin, is produced during the aerobic fermentation of suitable aqueous nutrient media under controlled conditions via the inoculation with the organism, *Streptomyces cattleya*. Aqueous media, such as those employed for the production of other antibiotics are suitable for producing N-acetyl thienamycin. Such media contain sources of carbon, nitrogen and inorganic salts assimilable by the microorganism.

In general, carbohydrates such as sugars, for example, glucose, fructose, maltose, sucrose, xylose, mannitol and the like and starches such as grains, for example, oats, rye, cornstarch, corn meal and the like can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the Examples are merely illustrative of the wide variety of media which may be employed, and are not intended to be limitative.

The fermentation is carried out at temperatures ranging from about 20° C. to 37° C.; however, for optimum results it is preferable to conduct the fermentation at temperatures of from about 22° C. to 30° C. The pH of the nutrient media suitable for growing the *Streptomyces cattleya* culture and producing N-acetyl thienyamycin can vary from about 6.0 to 8.0.

Although the novel antibiotic N-acetyl thienamycin is produced by both surface and submerged cultures, it is preferred to carry out the fermentation in the submerged state.

A small scale fermentation of the antibiotic is conveniently carried out by inoculating a suitable nutrient medium with the antibiotic-producing culture and, after transfer to a production medium, permitting the fermentation to proceed at a constant temperature of about 24° C. on a shaker for several days.

The fermentation is initiated in a sterilized flask of medium via one or more stages of seed development.

The nutrient medium for the seed stage may be any suitable combination of carbon and nitrogen sources. The seed flask is shaken in a constant temperature chamber at about 28° C. for one or two days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 3 to 5 days while agitating and/or aerating the nutrient medium and maintaining the temperature at about 24° C. This method of producing N-acetyl thienamycin is particularly suited for the preparation of large quantities of the antibiotic.

PHYSICAL AND CHEMICAL PROPERTIES OF N-ACETYL THIENAMYCIN

An NMR spectrum at 100 MHz of N-acetyl thienamycin revealed the following peaks:

The antibiotic is localized by bioautography on *Vibrio percolans*, ATCC 8461 (without intervening drying of the paper), and migration is measured from the point of application to the center of the zone of inhibition.

Thin layer chromatography using cellulose-coated sheets and an ethanol: $H_2O$, 70:30 solvent system reveals an $R_f$ for N-acetyl thienamycin obtained by fermentation and obtained by acetylating thienamycin of 0.7, as detected by bioautography on *Vibrio percolans*, ATCC 8461. The $R_f$ value refers to the distance from the origin to the center of bioactivity divided by the distance from the origin to the solvent front.

The IR spectrum of N-acetyl thienamycin is set forth in FIG. 1.

N-Acetyl thienamycin is believed to have a molecular structure as follows:

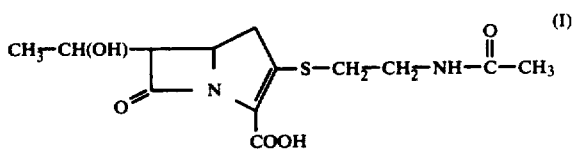

(I)

N-Acetyl thienamycin is further characterized by the following antibiotic spectrum profile. The test employs the Bauer-Kirby disc diffusion method modified only in respect to the 2 mm. agar depth employed here. The results, expressed in terms of the diameter in millimeters of the zone of inhibition are as set forth in Table 3. Table 3 sets forth the antibiotic spectrum profile of N-acetyl thienamycin and that of the material obtained by acetylating thienamycin.

TABLE 3

| Test Organism | MERCK No. | ATCC No. | Antibiotic Resistance* | N-Acetyl Thienamycin[a] 9.85 μg/disc | N-Acetyl Thienamycin[b] 10.35 μg/disc.** |
|---|---|---|---|---|---|
| *Staphylococcus aureus* | MB2985 | — | — | 37 | 37 |
|  | MB2314 | — | P | 37 | 37 |
| *Bacillus subtilis* | MB 964 | 6633 | — | 43 | 44.5 |
| *Escherichia coli* | MB2884 | — | — | 31.5 | 31.5 |
|  | MB2964 | — | P,C | 28.5 | 29.5 |
|  | MB2482 | — | P | 28 | 28 |
| *Klebsiella pneumoniae* | MB2921 | — | P | 28 | 28.5 |
|  | MB2922 | — | P | 27 | 30 |
| *Enterobacter cloacae* | MB2646 | — | P,C | 26.5 | 27 |
|  | MB2647 | — | — | 29 | 29 |
| *Proteus mirabilis* | MB2830 | — | P,C | 25 | 26 |
| *Proteus morganii* | MB2833 | — | P,C | 25.5 | 25 |
| Serratia | MB2840 | — | P,C | 27 | 27 |
| *Pseudomonas aeruginosa* | MB2824 | — | P,C | 23 | 24 |
|  | MB2835 | — | P,C | 11 (hazy) | 11 (hazy) |
|  | MB3286 | — | P,C | 0 | 0 |

*P = Penicillins as represented by ampicillin
C = Cephalosporins as represented by cephalothin
**Weight calculations based on an assumed $E^{1\%}_{1\ cm.,\ 301\ nm}$ = 290 and a hydroxylamine extinguishability of 96% for pure material.
[a]Prepared by fermenting *Streptomyces cattleya*.
[b]Prepared by acetylating thienamycin.

δ1.27, d, 3H, J ≃6.5; δ1.98, S, 3H; δ2.94 m, 2H; δ3.17, m, 2H; δ3.38, t, 2H, J ≃6.5; δ3.38, m, 1H; δ4.20, m, 2H.

The NMR spectrum of a combined solution of N-acetyl thienamycin obtained by fermentation and obtained by acetylating thienamycin is indistinguishable from those of the individual solutions. From the λ max dependence on pH, a $pK_a$ of 3.3±0.1 for a COOH group in N-acetyl thienamycin has been determined.

Upon paper electrophoresis in 0.1 M potassium phosphate buffer, pH 7, employing Schleicher and Schuell No. 2043-B paper at a voltage gradient of 50 v/cm., both N-acetyl thienamycin obtained by fermentation and obtained by acetylating thienamycin migrate 2.7 cm. toward the anode over a 20 minute period at 10° C.

N-Acetyl thienamycin exhibits in vivo activity against gram-negative and gram-positive organisms and hence is useful in controlling bacterial infections in humans and animals. In determining the in vivo activity, N-acetyl thienamycin is dissolved in and diluted with 0.01 M sodium phosphate, pH 7.0, to provide five four-fold concentrations of drug for testing. Female white Swiss mice, averaging about 21 g. in weight, were infected intraperitoneally with the test organism suspended in broth. The numbers of organisms injected were determined by standard plate-count techniques. At the time of infection, and again 6 hours later, certain of the mice were treated intraperitoneally with the antibiotic. Five mice were used for each concentration of drug tested. Controls of five mice for each of several dilutions of the infecting culture were included in each test in order to calculate the numbers of organisms that were lethal to 50% of the infected, untreated mice ($LD_{50}$). This calculation was made using survival data of the seventh day after infection, at which time the amount of drug that should protect 50% of the infected mice ($ED_{50}$) also was calculated.

All animals receiving this challenge and not treated with antibiotic died within 48 hours of the infection. The efficacy of N-acetyl thienamycin is recorded in Table 4:

TABLE 4

| | Efficacy Studies (mice)[a] | | |
|---|---|---|---|
| Organism | No. $LD_{50}$ | Route of treatment, doses | $ED_{50}$ mg./kg./dose[c] |
| Staph aureus 2949 | 13 | i.p. × 2[b] | 0.050 |

[a]CD-1, female mice, body wt. 21 g.
[b]Indicates treatment at the time of infecting dose and again 6 hours later.
[c]Wt. of N-acetyl thienamycin based on estimated $E^{1\%}_{1\ cm.,\ 301\ nm} = 290$ and hydroxylamine extinguishability of 96% for pure material.

N-Acetyl thienamycin is a valuable antibiotic active against various gram-positive and gram-negative bacteria and, accordingly, finds utility in human and veterinary medicine. The compound of this invention can be used as an antibacterial drug for treating infections caused by gram-positive or gram-negative bacteria, for example against *Staphylococcus aureus*, *Proteus mirabilis*, *Escherichia coli*, *Klebsiella pneumoniae*, and *Enterobacter cloacae*. The antibacterial material of the invention may further be utilized as an additive to animal feedingstuffs, for preserving foodstuffs and as a disinfectant. For example, it may be employed in aqueous compositions in concentrations ranging from 0.1 to 100 parts or preferably in concentrations ranging from about 1 to 10 parts of antibiotic per million parts of solution in order to destroy and inhibit the growth of harmful bacteria on medical and dental equipment and as a bactericide in industrial applications, for example in water-based paints and in the white water of paper mills to inhibit the growth of deleterious bacteria.

The antibiotic of this invention may be used in any one of a variety of pharmaceutical preparations as the sole active ingredient or in combination either with one or more other antibiotics or with one or more pharmacologically active substances. As an example of the former, an aminocyclitol antibiotic such as gentamicin may be co-administered in order to broaden the antimicrobial spectrum and to minimize any chance that resistant organisms will emerge. As an example of the latter, diphenoxylate and atropine may be combined in dosage forms intended for the therapy of gastroenteritis. The antibiotic may be employed in capsule form or as tablets, powders or liquid solutions or as suspensions or elixirs. It may be administered orally, topically, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; nonaqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like.

In veterinary medicine, such as in the treatment of chickens, cows, sheep, pigs and the like, the composition may, for example, be formulated as an intramammary preparation in either long acting or quick-release bases.

The dosage schedule and route of administration depends to a large extent upon the condition of the subject being treated, the weight of the host, the susceptibility of the infecting organism and the state of infection; the parenteral route being preferred for systemic infections and the oral route for intestinal infections.

In the treatment of bacterial infections in man, the compound of this invention is administered orally or parenterally, in accordance with conventional procedures for antibiotic administration, in an amount of from about 2 to 600 mg./kg./day and preferably about 5 to 100 mg./kg./day in preferably divided dosage, e.g. three to four times a day. They may be administered in dosage units containing, for example, 25, 250, 400, 800 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in any given instance will depend upon the type and severity of infection to be treated, and that smaller doses will be employed for pediatric use, all of such adjustments being within the skill of the practitioner in the field.

Included in this invention are the non-toxic, pharmaceutically acceptable salts of N-acetyl thienamycin, for example, the pharmacologically acceptable salts formed with inorganic and organic bases; which include, for example, metal salts derived from alkali metal or alkaline earth metal hydroxides, carbonates or bicarbonates such as those derived from sodium, potassium, ammonium and calcium and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower-alkylamino substituted lower alkanols, amino-, polyamino- and guanidino-substituted lower alkanoic acids and nitrogen-containing heterocyclic amines. Representative examples include salts derived from sodium hydroxide, ammonium hydroxide, sodium carbonate, sodium bicarbonate, potassium carbonate, potassium hydroxide, calcium carbonate, trimethylamine, triethylamine, piperidine, N-ethylpiperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

The salts of the compound of the present invention may be prepared by conventional methods well known in the art. For example, the mono-salts such as monosodium salt obtained by treating one equivalent of sodium hydroxide with one equivalent of the product (I) in a suitable solvent. Also mixed salts with divalent cations may be prepared by combining one mole of a divalent base with one mole of the product (I) plus one equivalent of another acid. Alternatively, salts may be obtained by treating one equivalent of a base having a divalent cation, such as calcium hydroxide, with one equivalent of the product (I). The salts of this invention are pharmacologically acceptable non-toxic derivatives which can be used as the active ingredient in suitable unit-dosage pharmaceutical forms. Also, they may be combined with other drugs to provide compositions having a broad spectrum of activity.

The antibiotic containing fermentation broths produced in accordance with the procedures described herein have activities ranging from about 0.1 to 4 µg. per ml. Antibiotic preparations can be purified and the antibiotic recovered by a number of procedures. One such procedure comprises passing filtered broth containing N-acetyl thienamycin through a column of strong cation exchange resin. Illustrative of such resins are those of the sulfonate type having a styrenedivinylbenzene matrix, for example the polystyrene nuclear sulfonic acid resin Dowes 50×2 (manufactured by Dow Chemical Co., Midland, Mich.), on the sodium cycle. Other representative members of the class of strong cation exchange resins include the following: Dowex 50×4, Dowex 50×8 (manufactured by Dow Chemical Co., Midland, Mich.), Amberlite IR120 (manufactured by Rohm & Haas, Co., Philadelphia, Pa.), Duolite C25D (manufactured by Chemical Process Co., Redwood City, Calif.), Permutit Q (manufactured by Permutit Co., Birmingham, N.J.), Ionac C-249 (manufactured by Ionac Chemical Co., Birmingham, N.J.) and Amberlite 200.

The spent from the cation exchange resin containing the antibiotic N-acetyl thienamycin can be further purified, if desired, by other purification procedures. It may be noted that thienamycin itself remains adsorbed on the strong cation exchange resin. Accordingly, the procedure for separating these two compounds is clearly distinguishable.

One such procedure comprises adsorbing N-acetyl thienamycin on a strongly basic anion exchange resin. Illustrative of such strongly basic anion exchange resins are those having a styrene-divinylbenzene matrix, for example the polystyrene nuclear quaternary ammonium resin Dowex 1×2, (manufactured by Dow Chemical Co., Midland, Mich.), on the chloride cycle. Other representative members of this class of strongly basic exchange resins include the following: Duolite A-40, A-42, A-101, A-102 and A-114 (manufactured by Chemical Process Co., Redwood City, Calif.); Amberlite IRA-400, IRA-401 and IRA-410 (manufactured by Rohm and Haas, Washington Square, Philadelphia 5, Pa.). The antibiotic N-acetyl thienamycin contained in the eluate can be further purified by passing it through a column packed with an acrylic ester polymer of intermediate polarity such as XAD-7 or 8 or through polystyrene, non-polar, hydrophobic crosslinked divinyl benzene polymers such as XAD-1, 2 and 4, preferably XAD-2. (XAD-1, 2, 4, 7 and 8 are manufactured by Rohm and Haas, Washington Square, Philadelphia, 5, Pa.).

A method of obtaining further purified N-acetyl thienamycin is by the use of gel filtration through polyacrylamide gel having a pore size which excludes molecules having a molecular weight greater than 1800 such as Bio-Gel P-2 (manufactured by Bio.Rad, Richmond, Calif.).

A preferred method for recovering purified N-acetyl thienamycin is to pass a solution of the antibiotic, such as the filtered fermentation broth, the pH of which has been adjusted between 4 to 5 through a column containing a strong cation exchange resin of the sulfonate type in the sodium cycle (Dowex 50×4). The collected spent may be further purified by a sequence of processes involving the following chromatographic media: anion exchange resins of the polystyrene-trimethylammonium type (e.g. Dowex 1×2 in the chloride cycle), polymeric absorbents (e.g. XAD-2, a polystyrene resin), Dowex 1×4 in the chloride cycle and gel permeation resins (e.g. Bio-Gel P-2, a polyacrylamide resin). The bioactivity of the eluates is measured by assaying the eluate using *Staphylococcus aureus* ATCC 6538P as the assay organism or as purity permits, by hydroxylamine-extinguished absorbance. A preferred method of obtaining N-acetyl thienamycin from fermentation broth is set forth in Table 5.

N-acetyl thienamycin, the antibiotic of the present invention, may also be prepared by acetylation of thienamycin. Acetylation is carried out by acetyl halide or preferably by acetic anhydride. Thienamycin is dissolved in a suitable inert solvent such as DMF and treated with an excess of acetylating agent at a temperature from $-10°$ C. to $25°$ C. but preferably at about $0°$ C. The reaction is complete in about 1 minute to about 1 hour. A reaction time of about 10 minutes at $0°$ C. is usually sufficient. The crude N-acetyl thienamycin obtained by acetylating thienamycin can be purified by the process described above for purifying filtered fermentation broths containing N-acetyl thienamycin.

A preferred method of purifying N-acetyl thienamycin obtained by acetylation is to adsorb the crude material on an anion exchange resin such as Dowex 1×4 in the chloride cycle and elute with an aqueous salt solution. A suitable aqueous salt solution contains sodium chloride, ammonium chloride and ammonia preferably in the concentration of about 0.07 M, 0.005 M and 0.0001 M, respectively. The fractions containing the product are combined and concentrated. The concentrate may be further purified by gel filtration through a polyacrylamide gel. A preferred gel is Bio-Gel P-2 eluted with deionized water.

The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of functionally equivalent products should be construed as constituting an analogous method. The described processes are capable of wide variation and modification and any minor departure or extension is considered as being within the skill of the artisan and as falling within the scope of this invention.

8 g./l. of Difco Nutrient Broth and 2 g./l. of yeast extract in distilled water (hereinafter designated NBYE). The culture is incubated overnight on a rotary shaker at 28° C. This culture is used to inoculate the surface of slants containing 1.5% agar in NBYE, and the inoculated slants are incubated overnight at 28° C. and then stored in a refrigerator.

The refrigerated slants prepared from a single lyophilized culture are used for up to four weeks from their preparation, as follows: A loop of inoculum from the slant is dispersed in 50 ml. of NBYE contained in a 250 ml. Erlenmeyer flask. The culture is incubated overnight on a rotary shaker at 28° C., and is then diluted to a density giving 50% transmittance at 660 nm. A 33.2 ml. portion of this diluted culture is added to 1 liter of NBYE containing 15 g. of agar and maintained at 46° C. The inoculated agar-containing medium is poured into 100×15 mm. plastic petri dishes, 5 ml. per dish, chilled, and maintained at 2°–4° C. for up to 5 days before using.

Plates containing *Staphylococcus aureus* ATCC 6538P are prepared as follows:

An overnight growth of the assay organism, *Staphylococcus aureus* ATCC 6538P, in nutrient broth plus 0.2% yeast extract is diluted with nutrient broth plus 0.2% yeast extract to a suspension having 55% transmittance at a wavelength of 660 nm. This suspension is added to

TABLE 5
OUTLINE OF PURIFICATION PROCESS FOR ANTIBIOTIC N-ACETYL THIENAMYCIN

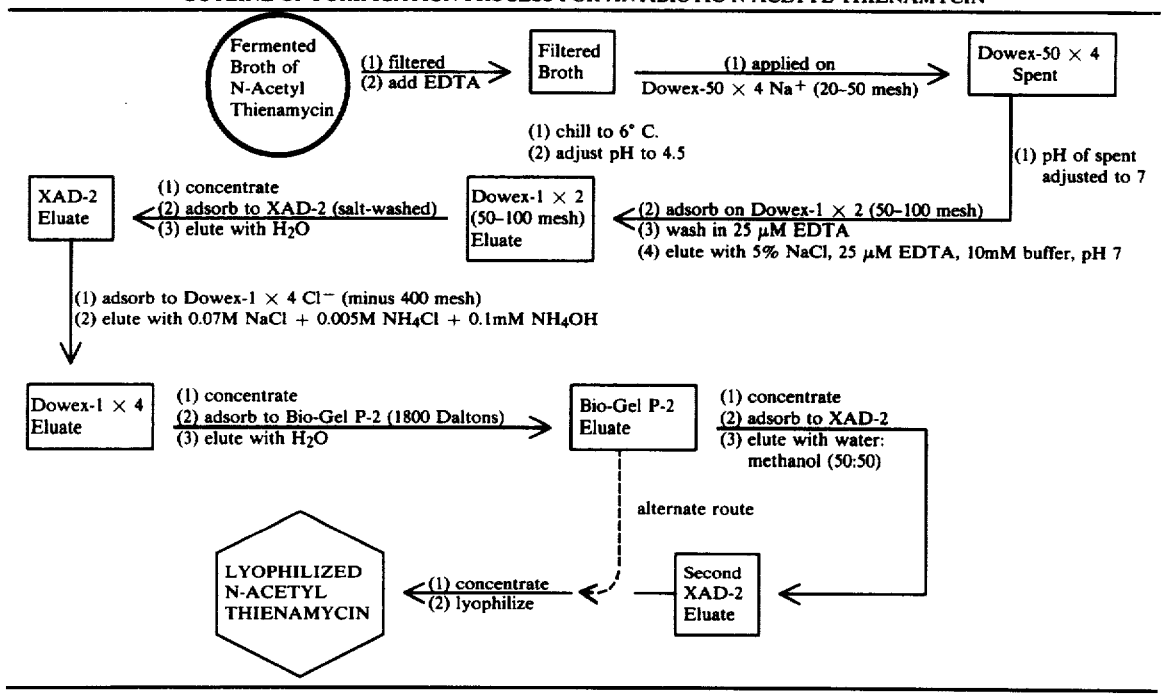

ASSAY PROCEDURES FOR ANTIBIOTIC N-ACETYL THIENAMYCIN

I. Bioassay

Assays of antibacterial activity are run according to the following disc-diffusion method using either *Vibrio percolans* ATCC 8461 or *Staphylococcus aureus* ATCC 6538P as tester organism.

Plates containing *Vibrio percolans* ATCC 8461 are prepared as follows:

A lyophilized culture of *Vibrio percolans* ATCC 8461 is suspended in 15 ml. of a sterilized medium containing Difco nutrient agar supplemented with 2.0 g./l. Difco yeast extract at 47° C. to 48° C., to make a composition containing 33.2 ml. of the suspension per liter of agar. Five ml. of this suspension is poured into petri dishes of 85 mm. diameter, and these plates are chilled and held at 4° C. until used (5 day maximum).

Samples of antibiotic to be assayed are diluted to an appropriate concentration in phosphate buffer at pH 7. Filter paper discs, ¼ or ½ inch diameter, are dipped into the test solution and placed on the surface of the assay plate. The plates are incubated at 37° C. overnight, and the zone of inhibition is measured as mm. diameter. The zone of inhibition measured in mm. determines relative potencies.

II. Hydroxylamine-extinguishable absorbance

The proportion of absorbance measured at 301 nm which can be attributed to the antibiotic content in impure samples is determined by the selective extinction of this absorbance (with concomitant inactivation of antibiotic activity) upon reaction with dilute hydroxylamine.

Samples containing antibiotic to be tested are prepared in 0.01 M potassium phosphate buffer at pH 7 to have an initial $A_{301}$ between 0.1 and 1.0. Freshly prepared, neutralized hydroxylamine ($NH_2OH\cdot HCl$ plus NaOH to a final pH of 7) is added to a final concentration of 10 mM, and the reaction is allowed to progress at room temperature for at least 30 minutes. The resulting $A_{301}$ when subtracted from the initial reading (after correction for dilution by added reagent) yields the hydroxylamine-extinguishable absorbance. Solutions of pure N-acetyl thienamycin show a hydroxylamine-extinguishable absorbance of 96.0%.

EXAMPLE 1

A tube of lyophilized culture of *Streptomyces cattleya* NRRL 8057 is opened aseptically and the contents suspended in a tube containing 0.7 ml. of sterile Davis salts having the following composition:

| Davis Salts | | |
|---|---|---|
| Sodium citrate | 0.5 | g. |
| $K_2HPO_4$ | 7.0 | g. |
| $KH_2PO_4$ | 3.0 | g. |
| $(NH_4)_2SO_4$ | 1.0 | g. |
| $MgSO_4\cdot 7H_2O$ | 0.1 | g. |
| Distilled $H_2O$ | 1000 | ml. |

A 0.2 ml. portion of this suspension is used to inoculate a culture slant of Medium A (plus agar) having the following composition:

| Medium A | | |
|---|---|---|
| Yeast Autolysate (Ardamine*) | 10.0 | g. |
| Glucose | 10.0 | g. |
| +Phosphate Buffer | 2.0 | ml. |
| $MgSO_4\cdot 7H_2O$ | 0.05 | g. |
| Distilled $H_2O$ | 1000 | ml. |
| pH: adjust to 6.5 using NaOH | | |
| *Ardamine: Yeast Products Corporation | | |
| +Phosphate Buffer Solution | | |
| $KH_2PO_4$ | 91.0 | g. |
| $Na_2HPO_4$ | 95.0 | g. |
| Distilled $H_2O$ | 1000 | ml. |
| For Slants: add agar - 25.0 g./l. | | |

The inoculated slant is incubated for 8 days at 28° C. and then stored at 4° C.

A portion of the spores and aerial mycelia of this slant is used to inoculate a baffled 250 ml. Erlenmeyer seed flask containing 50 ml. of Medium A (without agar). This seed flask is shaken at 28° C. on a 220 rpm shaker (2" throw) for two days at which time the growth is satisfactory.

Fifteen 250 ml. Erlenmeyer flasks, each containing 40 ml. of Medium B, are inoculated with 1 ml. per flask of the growth from the seed flask. The Medium B has the following composition:

| Medium B | | |
|---|---|---|
| Corn Meal | 20.0 | g. |
| Distiller's Solubles | 10.0 | g. |
| Soybean Meal | 15.0 | g. |
| Sodium Citrate | 4.0 | g. |
| $CaCl_2\cdot 2H_2O$ | 0.5 | g. |
| $MgSO_4\cdot 7H_2O$ | 0.1 | g. |
| $CoCl_2\cdot 6H_2O$ | 0.01 | g. |
| $FeSO_4\cdot 7H_2O$ | 0.01 | g. |
| **Polyglycol 2000 | 0.25% | by Vol. |
| Distilled $H_2O$ | 1000 | ml. |
| pH: adjust to 6.5 using NaOH | | |

**Polyglycol 2000: Dow Chemical Co.

These 15 production flasks are shaken at 28° C. on a 220 rpm shaker (2" throw) for 53 hours. At harvest (53 hours age) the broth from the 15 flasks is pooled and an aliquot is centrifuged for assay. Prior to assay the pH of the centrifuged broth is adjusted to 6.5 from 5.9 with NaOH.

Assays are run on *Staphylococcus aureus* ATCC 6538P and *Vibrio percolans* ATCC 8461 assay plates using ¼" discs dipped in the supernatant of centrifuged broth.

Assay results are as follows:

| ATCC 6538P Activity (mm. zone) | ATCC 8461 Activity (mm zone) |
|---|---|
| 39/44 SH | 35/44 SH |

SH = slightly hazy

Two-hundred mls. of filtered broth is adjusted to pH 8.0 and adsorbed on 10 ml. of Dowex 1×2 resin in the chloride cycle at 2 ml./min., collecting the spent effluent stream in 10×20 ml. fractions.

The adsorbate is eluted with 90% methanol; 10% water; 3% ammonium-chloride v/v/w, collecting the eluate in 10×5 ml. fractions. Eluate fractions 1 through 6 are combined and concentrated in vacuo to remove the methanol. The concentrate is assayed by the disc-diffusion procedure using a ¼ inch diameter disc containing 100 μl. antibiotic solution against *Staphylococcus aureus* fMB-2985 and gives a zone size of 28 mm.

Assay plates of MB-2985 are prepared as follows:

An overnight culture of MB-2985 grown in brain heart infusion medium at 37° C. with shaking, is diluted 20,000 x and swabbed onto the surface of 10 ml. brain heart infusion agar contained in an 85 mm. diameter petri dish. Discs of ¼ inch diameter containing 100 μl. antibiotic solution are placed on the plates which are then incubated 18 hours at 37° C. Zones of inhibition are read in mm.

EXAMPLE 2

A tube of lyophilized culture of *Streptomyces cattleya* NRRL 8057 is opened aseptically and the contents is used to inoculate a baffled 250 ml. Erlenmeyer seed flask containing 50 ml. of Medium A having the following composition:

| Medium A | | |
|---|---|---|
| Yeast Autolysate (Ardamine*) | 10.0 | g. |
| Glucose | 10.0 | g. |
| +Phosphate Buffer | 2.0 | ml. |
| $MgSO_4\cdot 7H_2O$ | 0.05 | g. |
| Distilled $H_2O$ | 1000 | ml. |
| pH: adjust to 6.5 using NaOH | | |
| *Ardamine: Yeast Products Corporation | | |

-continued

| +Phosphate Buffer Solution | |
|---|---|
| KH$_2$PO$_4$ | 91.0 g. |
| Na$_2$HPO$_4$ | 95.0 g. |
| Distilled H$_2$O | 1000 ml. |

This seed flask is shaken at 28° C. on a 220 rpm shaker (2" throw) for two days at which time the growth is satisfactory.

Fifteen 250 ml. Erlenmeyer flasks, each containing 40 ml. of Medium B, are inoculated with 1 ml. per flask of the growth from the seed flask. The Medium B has the following composition:

| Medium B | | |
|---|---|---|
| Corn Meal | 20.0 | g. |
| Distiller's Solubles | 10.0 | g. |
| Soybean Meal | 15.0 | g. |
| Sodium Citrate | 4.0 | g. |
| CaCl$_2$ . 2H$_2$O | 0.5 | g. |
| MgSO$_4$ . 7H$_2$O | 0.1 | g. |
| CoCl$_2$ . 6H$_2$O | 0.01 | g. |
| FeSO$_4$ . 7H$_2$O | 0.01 | g. |
| **Polyglycol 2000 | 0.25% | by Vol. |
| Distilled H$_2$O | 1000 | ml. |
| pH: adjust to 6.5 using NaOH | | |

**Polyglycol 2000: Dow Chemical Co.

These flasks are shaken at 28° C. on a 220 rpm shaker (2" throw) for three days with assays performed during the fermentation cycle. Assays are run on standard *Staphylococcus aureus* ATCC 6538P and *Vibrio percolans* ATCC 8461 assay plates using ¼" discs dipped in the supernatent of centrifuged broth. The pH of this broth is adjusted prior to assay as shown in the following table. The results are as follows:

| Age (Hours) | 48 | 53 | 72 |
|---|---|---|---|
| ATCC 6538P Activity | 33/39h | 31/38h | 21/27h |
| ATCC 8461 Activity | 35sh/46h | 36 sh/44h | 33sh/38h |
| pH, initial | 5.2 | 5.1 | 4.8 |
| pH, adjusted | 6.1 | 6.2 | 6.9 | sh = slightly hazy
h = hazy

At 53 hours age, the broths are pooled and filtered to yield 590 ml. of filtrate at pH 5.9. The pH of the filtrate is adjusted to pH 7.0 and 5.9 mg. of ethylenedinitrile tetraacetic acid (EDTA), is added.

A 580 ml. portion of the above filtrate, at pH 7.0, is adsorbed on 130 ml. of Dowex 1×2 resin in the chloride cycle collecting the spent stream in 2×290 ml. fractions. The adsorbate is then washed with 130 ml. of deionized water. The washed adsorbate is stored in the coldroom overnight and then eluted with 5% NaCl solution collecting 6×50 ml. fractions.

The percent recovery of initial bioactivity, determined by the disc plate method, is tabulated below:

| Fraction | *Vibrio percolans* ATCC 8461 | *Staph. aureus* ATCC 6538P |
|---|---|---|
| Eluate Fractions 1 to 5 | 26% | 1% |

Antibiotic N-acetyl thienamycin is found in fractions 1 to 5 of the NaCl eluate. Fraction 4 is assayed by the disc-diffusion procedure using ½ inch diameter discs containing 100 μl. antibiotic solution against *Staphylococcus aureus MB*-2985 and gives a zone size of 29 mm. Plates containing MB-2985 are prepared according to the process set forth in Example 1.

EXAMPLE 3

A tube of lyophilized culture of *Streptomyces cattleya* NRRL 8057 is opened aseptically and the contents suspended in 0.8 ml. of sterile Davis salts having the following composition:

| Davis Salts | |
|---|---|
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate four slants of Medium A (plus agar) having the following composition:

| Medium A | |
|---|---|
| Yeast Autolysate (Ardamine*) | 10.0 g. |
| Glucose | 10.0 g. |
| +Phosphate Buffer | 2.0 ml. |
| MgSO$_4$ . 7H$_2$O | 0.05 g. |
| Distilled H$_2$O | 1000 ml. |
| pH: adjust to 6.5 using NaOH | |
| *Ardamine: Yeast Products Corporation | |
| +Phosphate Buffer Solution | |
| KH$_2$PO$_4$ | 91.0 g. |
| Na$_2$HPO$_4$ | 95.0 g. |
| Distilled H$_2$O | 1000 ml. |
| For Slants: add agar - 25.0 g./l. | |

The inoculated slants are incubated for one week at 28° C. and then stored at 4° C.

Ten ml. of Medium A (without agar) is transferred aseptically to one of these slants, the spores and aerial mycelia scraped into suspension, and 1.2 ml. of this suspension used to inoculate three 2 liter baffled Erlenmeyer flask containing 500 ml. of Medium A (without agar). These seed flask are shaken at 28° C. on a 160 rpm shaker for 24 hours at which time the growth is satisfactory.

The growth from these seed flasks is pooled and used to inoculate a 756 liter stainless steel fermentor containing 467 liters of Medium A (without agar). This tank is operated at 28° C. using an agitation rate of 130 rpm and an airflow of 10 cu. ft. per minute for 24 hours. Defoamer, Polyglycol 2000 (Dow Chemical Corp.), is used as required but does not exceed 0.1%. pH determinations are made as follows:

| Age, Hours | 0 | 24 |
|---|---|---|
| pH | 6.3 | 6.4 |

Four hundred fifty-four liters of the growth in this seed tank is used to inoculate a 5,670 liter stainless steel fermentor containing 4,082 liters of Medium E, wherein Medium E has the composition:

| Medium E | | |
|---|---|---|
| Cerelose | 25.0 | g. |
| Corn Steep Liquor (wet basis) | 15.0 | g. |
| Distiller's Solubles | 10.0 | g. |
| Cottonseed Media (Pharmamedia) | 5.0 | g. |

-continued

| Medium E | | |
|---|---|---|
| CoCl$_2$ . 6H$_2$O | 0.01 | g. |
| CaCO$_3$ (after pH adjustment) | 3.0 | g. |
| Polyglycol 2000 | 0.25% | |
| Tap water | 1000 | ml. |
| pH: adjust to 7.3 using NaOH | | |

This tank is run at 24° C. using an agitation rate of 70 rpm and an airflow of 54.3 cu. ft. per minute for 138 hours. Additional defoamer, Polyglycol 2000, is added as required, but does not exceed 0.1%. Antibacterial assays are run and the data is as follows:

| Age | pH | ATCC No. 6633 (¼" disc.) (mm.) |
|---|---|---|
| 0 | 6.9 | 0 |
| 24 | 6.3 | 0 |
| 36 | 6.0 | 0 |
| 48 | 5.9 | 0 |
| 60 | 6.0 | 23 |
| 72 | 5.9 | — |
| 84 | 6.0 | 21 |
| 96 | 6.2 | — |
| 108 | 6.5 | 35 |
| 120 | 6.6 | 36 |
| 132 | 6.7 | 41 |
| 138 | 6.7 | 39 |

The 4082 liters of fermentation broth is filtered using a 30-inch filter press and a filter aid admix to the extent of 4% w/v. A 46 g. amount of ethylenedinitrile tetraacetic acid (EDTA), sodium salt is added to the filtrate. The filtrate is cooled to 6° C., adjusted to pH 4.5±0.2 and maintained at 6° C. The cold filtrate is applied to a 480 liter column of Dowex 50×4 Na$^+$, 20–50 mesh at about 48 l./minute. After a 1400 liter forerun has passed through, 18.9 liters of spent is collected, the pH of the spent is adjusted to 7.08 with NaOH, and stored at 5° C.

A 3.8 cm. diameter column packed with 300 ml. of Dowex 1×2, 50–100 mesh, resin in the chloride cycle is prepared and washed with 600 ml. of deionized water at 5° C. Four liters of the cold Dowex 50×4 spent is passed through the column at the rate of 30 ml./minute. The column is washed with 300 ml. 25 μM EDTA. The antibiotic, N-acetyl thienamycin, is eluted at 5° C. at the rate of 15 ml./minute with 900 ml. 5% NaCl solution containing 0.01 M potassium phosphate buffer, pH 7.0, and 25 μM EDTA. Fourteen fractions of 75 ml. are collected and assayed for biological activity by the disc-diffusion procedure. Eluate fractions 3 through 9, comprising 525 ml. are pooled and concentrated under vacuum to 115 ml. The concentrate contains 65% of the total bioactive material applied on the Dowex 1×2 Cl$^-$ column.

The Dowex 1×2 Cl$^-$ eluate concentrate is applied at 5° C. on a 3.8 cm. diameter column packed with 450 ml. prewashed XAD-2. The XAD-2 is prewashed column-wise successively with 4 column volumes: (1) 0.001 M EDTA, (2) 1 N NaOH, (3) deionized H$_2$O, (4) 1 N HCl, (5) deionized H$_2$O, (6) methanol, (7) acetone, (8) deionized water and prior to use with 2250 ml. 5% NaCl solution containing 25 μM EDTA.

After the sample is applied to the column, it is followed by two 25 ml. portions of H$_2$O. The column is developed at 5° C. with deionized H$_2$O at a flow rate of 10 ml./minute. The first fraction contains 400 ml. and 11 additional fractions of 75 ml. are collected. The pH of each fraction is adjusted to between 6.9 and 7.13 with 1 N NaOH or 1 N HCl. Fractions 3 to 9, containing 46% of the total bioactive material applied to the XAD-2 column, are combined and have a total volume of 490 ml. A sample of 45 ml. is removed for bioassays by the standard disc-diffusion procedure against Staphylococcus aureus ATCC 6538P. The remaining 445 ml. is concentrated under vacuum to 50 ml.

The 50 ml. XAD-2 eluate concentrate is pumped at 5° C. onto a 1.5 cm. column packed with 40 ml. prewashed Dowex 1×4 Cl$^-$, minus 400, at 5° C. and at a rate of 1 ml./min. The Dowex 1×4 Cl$^-$, minus 400 (defined by decanting from water) resin is washed column-wise prior to use with 240 ml. 0.2 M NaCl containing 0.005 M NH$_4$Cl and 0.1 mM NH$_4$OH at the rate of 1 ml./minute and then with 120 ml. deionized water at the same rate.

After the sample is applied to the column, it is followed by two, 5 ml. portions of deionized water. The column is developed at 5° C. at the rate of 0.92 ml./minute with 0.07 M NaCl containing 0.005 M NH$_4$Cl and 0.1 mM NH$_4$OH. Fractions of 8.6 to 9.3 ml. are collected. Fractions obtained after 600 ml. of eluate have been collected and ending with 710 ml. are pooled and contain 98% of the total bioactive material applied on the Dowex 1×4 column. This pool is concentrated under vacuum to 2 ml.

The Dowex 1×4 concentrate is applied to a 2.2 cm. diameter column packed with 225 ml. Bio-Gel P-2, 200–400 mesh, with an exclusion limit of 1800 Daltons (defined prior to use by decantation from distilled water).

The Bio-Gel P-2 column is washed prior to use with 225 ml. 1 M NaCl followed by 100 ml. deionized water. The column is developed with 5° C. deionized water at the rate of 1 ml./minute, and two ml. fractions are collected. Fractions from 104 ml. to 128 ml. eluate, containing 83% of the bioactivity applied to the Bio-Gel P-2 column, are combined and concentrated to 1.58 ml.

A 50 ml. XAD-2 column (1.6 cm.×27 cm.) is prepared and prewashed column-wise with 200 ml. of 1 mM EDTA, 1 N NaOH, deionized water, 1 N HCl, deionized water, methanol, acetone, and deionized water. The Bio-Gel P-2 concentrate containing 44.4 hydroxylamine-extinguishable optical density units is applied to the XAD-2 column at 5° C. and is followed by two, 2 ml. portions of deionized water. The column is washed with deionized water at the rate of 1 ml./minute until the UV absorbance at 300 nm of the washings is reduced to 0.060. The column is eluted with 50% methanol in deionized water at the rate of 1 ml./minute and 1 ml. fractions are collected. Fractions having absorbance at 300 nm over 0.1 are combined and concentrated under vacuum to give the product, N-acetyl thienamycin containing 11.6 hydroxylamine-extinguishable O.D. units.

EXAMPLE 4

A tube of lyophilized culture of Streptomyces cattleya NRRL 8057 is opened aseptically and the contents suspended in 0.8 ml. of sterile Davis salts having the following composition:

| Davis Salts | |
|---|---|
| Sodium citrate | 0.5 g. |
| K$_2$HPO$_4$ | 7.0 g. |
| KH$_2$PO$_4$ | 3.0 g. |

-continued

| Davis Salts | |
|---|---|
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate four slants of Medium A (plus agar) having the following composition:

| Medium A | |
|---|---|
| Yeast Autolysate (Ardamine*) | 10.0 g. |
| Glucose | 10.0 g. |
| +Phosphate Buffer | 2.0 ml. |
| MgSO$_4$ . 7H$_2$O | 0.05 g. |
| Distilled H$_2$O | 1000 ml. |
| pH: adjust to 6.5 using NaOH | |
| *Ardamine: Yeast Products Corporation | |
| +Phosphate Buffer Solution | |
| KH$_2$PO$_4$ | 91.0 g. |
| Na$_2$HPO$_4$ | 95.0 g. |
| Distilled H$_2$O | 1000 ml. |
| For Slants: add agar - 25.0 g./l. | |

The inoculated slants are incubated for one week at 28° C. and then stored at 4° C.

Ten ml. of Medium A is transferred aseptically to one of these slants, the spores and aerial mycelia scraped into suspension, and 1.2 ml. of this suspension used to inoculate three 2 liter baffled Erlenmeyer flask containing 500 ml. of Medium A (without agar). These seed flasks are shaken at 28° C. on a 160 rpm shaker for 24 hours at which time the growth is satisfactory.

The growth from these seed flasks is pooled and used to inoculate a 756 liter stainless steel fermentor containing 467 liters of Medium A (without agar). This tank is operated at 28° C. using an agitation rate of 130 rpm and an airflow of 10 cu. ft. per minute for 24 hours. Defoamer, Polyglycol 2000 (Dow Chemical Corp.), is used as required but does not exceed 0.1%. pH determinations are made as follows:

| Age, Hours | 0 | 24 |
|---|---|---|
| pH | 6.3 | 6.4 |

Four hundred fifty-four liters of the growth in this seed tank is used to inoculate a 5,670 liter stainless steel fermentor containing 4,082 liters of Medium E, wherein Medium E has the composition:

| Medium E | | |
|---|---|---|
| Cerelose | 25.0 | g. |
| Corn Steep Liquor (wet basis) | 15.0 | g. |
| Distiller's Solubles | 10.0 | g. |
| Cottonseed Media (Pharmamedia) | 5.0 | g. |
| CoCl$_2$ . 6H$_2$O | 0.01 | g. |
| CaCO$_3$ (after pH adjustment) | 3.0 | g. |
| Polyglycol 2000 | 0.25% | |
| Tap water | 1000 | ml. |
| pH: adjust to 7.3 using NaOH | | |

This tank is run at 24° C. using an agitation rate of 70 rpm and an airflow of 54.3 cu. ft. per minute for 138 hours. Additional defoamer, Polyglycol 2000, is added as required, but does not exceed 0.1%. Antibacterial assays are run and the data is as follows:

| Age | pH | ATCC No. 6633 (¼" disc.) (mm.) |
|---|---|---|
| 0 | 6.9 | 0 |
| 24 | 6.3 | 0 |
| 36 | 6.0 | 0 |
| 48 | 5.9 | 0 |
| 60 | 6.0 | 23 |
| 72 | 5.9 | — |
| 84 | 6.0 | 21 |
| 96 | 6.2 | — |
| 108 | 6.5 | 35 |
| 120 | 6.6 | 36 |
| 132 | 6.7 | 41 |
| 138 | 6.7 | 39 |

The 4082 liters of fermentation broth is filtered using a 30-inch filter press and a filter aid admix to the extent of 4% w/v. A 46 g. amount of ethylenedinitrile tetraacetic acid (EDTA), sodium salt is added to the filtrate. The filtrate is cooled to 6° C., adjusted to pH 4.5±0.2 and maintained at 6° C. The cold filtrate is applied to a 480 liter column of Dowex 50×4 Na$^+$, 20–50 mesh at about 48 l./minute. After a 1400 liter forerun has passed through, 18.9 liters of spent is collected, the pH of the spent is adjusted to 7.08 with NaOH, and stored at 5° C.

A 3.8 cm. diameter column packed with 300 ml. of Dowex 1×2, 50–100 mesh, resin in the chloride cycle is prepared and washed with 300 ml. of deionized water at 5° C. Four liters of the cold Dowex 50×4 spent is passed through the column at the rate of 30 ml./minute. The column is washed with 350 ml. 25 μM EDTA and then eluted at 5° C. with 900 ml., 5% NaCl solution containing 0.01 M Tris.HCl, pH 7, and 25 μM EDTA at the rate of 15 ml./minute. Fractions of 75 ml. are collected and assayed by the disc-diffusion procedure against *Staphylococcus aureus* ATCC 6538P. Fractions 4 to 10 containing 47% of the bioactivity applied are added to 42.5 ml. of the sample removed for bioassay from the first XAD-2 pool described in Example 3. These combined fractions are concentrated under vacuum to 100 ml., and the pH adjusted to 6.32 with HCl.

A 3.8 cm. diameter column packed with 450 ml. XAD-2 resin is prewashed column-wise successively with 4 column volumes: (1) 0.001 M EDTA, (2) 1 N NaOH, (3) deionized H$_2$O, (4) 1 N HCl, (5) deionized H$_2$O, (6) methanol, (7) acetone, (8) deionized water and washed prior to use with 2250 ml. 5% NaCl solution containing 25 μM EDTA. The above concentrate is applied to the XAD-2 column and is followed by two, 5 ml. portions of deionized water. The column is developed at 5° C. at the rate of 10 ml./minute with deionized water. The first fraction contains 40 ml., and subsequent fractions of 75 ml. are collected and assayed by the disc-diffusion process. Fractions 9 to 15, containing 22% of the bioactivity applied on the XAD-2 column are pooled and concentrated under vacuum to 56 ml.

A 21 cm.×1.7 cm. column packed with 40 ml. of Dowex 1×4 Cl$^-$, minus 400 mesh, (defined by decanting from water) is washed column-wise prior to use with 240 ml. 0.2 M NaCl containing 0.005 M NH$_4$Cl and 0.1 mM NH$_4$OH at the rate of 1 ml./minute and then with 120 ml. deionized water at the same rate.

The XAD-2 concentrate is applied on the column and is followed by two, 2 ml. portions of deionized water and then by two, 2 ml. portions of eluting buffer. The column is eluted at 5° C. with a solution 0.07 M NaCl containing 0.005 M NH$_4$Cl and 0.1 mM NH$_4$OH at the rate of 1 ml./minute. Fractions of 10 ml. are collected and assayed by the disc diffusion method. Eluate fractions from 544 ml. through 647 ml. containing an apparent 100% of the applied bioactivity are combined and concentrated under vacuum to 2.3 ml. The concentrate contains 36.4 hydroxylamine-extinguishable optical density units.

A 2.2 cm.×62 cm. column packed with 225 ml. Bio-Gel P-2, 200–400 mesh resin with an exclusion limit of 1800 Daltons is washed prior to use with 225 ml. 1 M NaCl followed by 100 ml. deionized water. The Dowex 1×4 concentrate is applied to the column and is followed by two, 2 ml. portions of deionized water. The column is developed at 5° C. with deionized water at the rate of 1 ml./minute and 2 ml. fractions are collected and assayed by the disc-diffusion procedure. Fractions from 124 ml. to 129 ml., containing 7.04 hydroxylamine-extinguishable O.D. units are combined and concentrated under vacuum to 2 ml. to give an aqueous solution of the product, N-acetyl thienamycin. Fractions from 117 to 123 ml. and 130 to 139 ml. are combined to give a solution of the product, N-acetyl thienamycin containing 13.7 hydroxylamine-extinguishable O.D. units.

EXAMPLE 5

Preparation of Thienamycin

A tube of lyophilized culture of *Streptomyces cattleya* NRRL 8057 is opened aseptically and the contents suspended in 50 ml. of sterile Medium A contained in a 250 ml. baffled Erlenmeyer flask. Medium A has the following composition:

| Medium A | | |
|---|---|---|
| Yeast Autolysate (Ardamine*) | 10.0 | g. |
| Glucose | 10.0 | g. |
| +Phosphate Buffer | 2.0 | ml. |
| MgSO$_4$ . 7H$_2$O | 0.05 | g. |
| Distilled H$_2$O | 1000 | ml. |
| pH: adjust to 6.5 using NaOH | | |
| *Ardamine: Yeast Products Corporation | | |
| +Phosphate Buffer Solution | | |
| KH$_2$PO$_4$ | 91.0 | g. |
| Na$_2$HPO$_4$ | 95.0 | g. |
| Distilled H$_2$O | 1000 | ml. |

The inoculated flask is shaken at 28° C. on a 220 rpm (2" throw) for 48 hours. Forty ml. of the 48-hour broth is removed aseptically and mixed with 40 ml. of sterile 20% (v/v) aqueous glycerol. Two ml. quantities of the resulting mixture are pipetted into sterile 1 dram vials which are then frozen and stored in the vapor phase of a liquid nitrogen freezer.

Frozen vial contents are used to inoculate a 250 ml. baffled Erlenmeyer flask containing 50 ml. of Medium A. This seed flask is shaken at 28° C. on a 160 rpm shaker at 28° C. for 24 hours.

Ten ml. portions from this seed flask are used to inoculate 2 liter baffled Erlenmeyer flasks containing 500 ml. of Medium A. These seed flasks are shaken on a 160 rpm shaker at 28° C. for 24 hours.

A one thousand ml. portion of the pooled contents of these seed flasks is used to inoculate a 756 liter stainless steel fermentor containing 467 liters of Medium A. This tank is operated at 28° C. using an agitation rate of 130 rpm and an airflow of 10 cu. ft. per minute for 24 hours. Polyglycol 2000 (Dow Chemical Corp.) is used as required as a defoamer but not to exceed 0.1%. Measurements of pH and dextrose are made and are as follows:

| Age (Hours) | 0 | 12 | 24 |
|---|---|---|---|
| pH | 6.4 | 6.4 | 6.6 |
| Dextrose mg./ml. | 8.1 | 8.1 | 8.1 |

Four hundred fifty-three liters of this growth are used to inoculate a 5670 liter stainless steel fermentor containing 4082 liters of Medium E, wherein Medium E has the composition:

| Medium E | | |
|---|---|---|
| Cerelose | 25.0 | g. |
| Corn Steep Liquor (wet basis) | 15.0 | g. |
| Distiller's Solubles | 10.0 | g. |
| Cottonseed Media (Pharmamedia) | 5.0 | g. |
| CoCl$_2$ . 6H$_2$O | 0.01 | g. |
| CaCO$_3$ (after pH adjustment) | 3.0 | g. |
| Polyglycol 2000 | 0.25% | |
| Tap water | 1000 | ml. |
| pH: adjust to 7.3 using NaOH | | |

This tank is operated at 24° C. using an agitation rate of 70 rpm and an airflow of 54.3 cu. ft. per minute for 144 hours. Defoamer, Polyglycol 2000, is added as required but does not exceed 0.1%. Centrifuged broth is assayed against *Staphylococcus aureus* ATCC 6538P by the standard disc-diffusion procedure. The results are tabulated in the table below under the heading "Antibiotic Activity vs ATCC 6538P". Assays are also run by the disc-diffusion procedure using ⅜-inch filter-paper discs and 10 ml. assay plates and the results tabulated in the table below under the heading "Antibiotic Activity (10 ml. plates)".

The 10 ml. assay plates are prepared as follows: An overnight growth of the assay organism, *Staphylococcus aureus* ATCC 6538P, in nutrient broth plus 0.2% yeast extract is diluted with nutrient broth plus 0.2% yeast extract to a suspension having 40% transmittance at a wavelength of 660 mμ. This suspension is added to Difco nutrient agar supplemented with 2.0 g./l. Difco yeast extract, at 47° C. to 48° C., to make a composition containing 33.2 ml. of the suspension per liter of agar. Ten ml. of this suspension are poured into petri plates of 85 mm. diameter, and the plates are chilled and held at 4° C. until used (5 day maximum).

| Age | pH | Dextrose mg./ml. | Antibiotic Activity vs ATCC 6538P (mm.) | Antibiotic Activity (10 ml. plates) (mm.) |
|---|---|---|---|---|
| 0 | 6.6 | 22.2 | | |
| 12 | 6.3 | 20.2 | | |
| 24 | 5.8 | 18.0 | | 0 |
| 36 | 6.0 | 13.2 | | 21.5 |
| 48 | 6.0 | 8.6 | | 21.5 |
| 60 | 5.7 | 6.4 | | 26.5 |
| 72 | 5.8 | 2.7 | | 25.5 |
| 84 | 6.2 | 0.3 | | 27.5 |
| 96 | 6.4 | 0.2 | | 36.0 |
| 108 | 6.4 | 0 | | 35.0 |
| 120 | 6.3 | | 41.5 | 37.0 |
| 132 | 5.8 | | | 37.5 |
| 144 | 5.9 | | 43.0 | 37.5 |

The 4,082 liters of fermentation broth is filtered using a 30 inch filter press and a filter aid admix to the extent of 4% w/v. A 12 g. amount of (ethylenedinitrilo) tetraacetic acid, sodium salt is added to the filtrate. The filtrate is cooled to 6° C., adjusted to pH 4.5±0.2 and maintained at 6° C. The cold filtrate is adsorbed on 480 l. of Dowex 50×4 Na+, 20–50 mesh at about 48 l./min. The adsorbate is washed with 480 l. of deionized water and then eluted with 2% aqueous pyridine at 24 l./min. and three fractions of 300 l., 520 l. and 240 l. are collected and assayed at pH 7.0. The assays indicate that the eluate fractions contain 4%, 16% and 6%, respectively of the bioactivity applied on the Dowex 50×4 Na+ column. Eluate fraction two is concentrated to 48 l. and adjusted to pH 7.

The 48 l. concentrate is adjusted to pH 7.3 and adsorbed on 76 l. of Dowex 1×2, 50 to 100 mesh, chloride cycle resin at 7.6 l./min. The resin is eluted with deionized water at the same rate. Four fractions are collected, two of 48 l., one of 70 l. and one of 48 l. The fractions are adjusted to pH 7 as collected. Assays indicate that 68% of the starting bioactivity is in the 70 l. fraction. This fraction is concentrated to 18 l. at pH 7.0 and filtered using a 0.45 micron Millipore Filter. The filtrate is tray freeze-dried to yield 99 grams of product having a potency of 310 units/mg. wherein one unit is defined as the amount which calculates to produce the same inhibition against *Staphylococcus aureus* ATCC 6538P using the disc-diffusion procedure as 1 μg. of cephalothin/ml. that zone of inhibition being between 16 and 21 mm. diameter.

Ten g. of the freeze-dried solids are taken up in 0.1 M 2,6-lutidine acetate buffer, pH 6.3. The solution, 125 ml. readjusted to pH 6.3 with acetic acid, is applied to a column of Dowex 50×8 (200–400 mesh) in the 2,6-lutidine cycle, 7.6×142 cm., which had previously been equilibrated with buffer, and developed with 0.1 M buffer at 25 ml./min. A 3 l. fore-cut is collected followed by 200 fractions of 20 ml. each. Every fourth fraction 36 through 192 is assayed at a dilution of 1:200. The bioactivity is contained in fractions 56 through 192, reaching a maximum in fractions 92 through 96. Fractions 80 through 136 are combined and 590 ml. of deionized water added to give 1760 ml. The pooled, diluted, solution containing 62% of the starting bio-activity applied on the Dowex 50×8 column, is freeze-dried.

The freeze-dried solids are dissolved in 0.1 M 2,6-lutidine acetate, pH 7.0 buffer. The solution, 27 ml., is applied to a column of Bio-Gel P-2 (200–400 mesh) 5×112 cm. which had previously been equilibrated with 0.1 M buffer. The gel is then developed with the same buffer at 10 ml./min.

The effluent stream is monitored with a Meccomatic recording differential refractometer. The development is continued until 105 fractions, 20 ml. each, are collected. Every fraction, 70 through 93, is assayed at a dilution of 1:300. The bio-activity is found in fractions 73 through 82, reaching a maximum in fractions 77 and 78. Fractions 75 through 80 are freeze-dried to obtain 90 mg. of antibiotic with an average potency of 10,000 units/mg.

The 90 mg. of freeze-dried solid is taken up into 4 ml. of 0.01 M potassium phosphate buffer, pH 7. This solution, containing 596 hydroxylamine-extinguishable optical density units (this measure of the thienamycin content being described in the section headed Assay) is applied on a 1.7 cm. diameter column packed with 90 ml. prewashed XAD-2 and equilibrated prior to use with 180 ml. of 0.01 M potassium phosphate buffer, pH 7, at 5° C. The XAD-2 is washed prior to use successively with (1) 5 volumes of 1 N NaOH followed by deionized $H_2O$ until effluent is neutral; (2) 5 volumes 1 N HCl followed by deionized $H_2O$ until the effluent is neutral; (3) 5 volumes each of methanol, acetone, 0.001 M EDTA tetrasodium, and finally distilled $H_2O$. Vacuum is applied to all solvents before use.

After the sample is applied on the column it is followed by two, 2 ml. portions of the phosphate buffer. The column is developed at 5° C. with the buffer at a flow rate of 2 ml./min. Four ml. fractions of eluate are collected. Fractions obtained after 100 ml. of eluate has been collected and ending with 253 ml. are combined and concentrated on a rotary evaporator under vacuum and below 10° C. to a volume of 6 ml.

This solution, containing 436 hydroxylamine-extinguishable optical density units, is applied on a 1.7 cm. diameter column packed with 90 ml. XAD-2 prewashed as above and equilibrated at 5° C. with distilled water. The sample is followed by two, 2 ml. portions of distilled water. The column is developed with distilled water at the rate of 2 ml./min. Four ml. fractions of eluate are collected. Fractions obtained after 100 ml. of eluate has been collected and ending with 151 ml. are pooled and concentrated on a rotary evaporator to a volume of 2.73 ml. and the solution lyophilized to yield 6.49 mg. of thienamycin. Fractions obtained between 152 ml. and 345 ml. are pooled and concentrated on a rotary evaporator to a volume of 3.34 ml. and lyophilized to yield 11.53 mg. of thienamycin. These fractions contain a total of 369 hydroxylamine-extinguishable optical density units. This represents a 3.1 fold purification over the material applied to the first XAD-2 column and yields a calculated potency of 31,000 units/mg. Spectrophotometric analysis of a sample of this product shows an $E_{1\ cm.}^{1\%} = 253$ when measured in phosphate buffer, pH 7, at 297 nm.

A ten g. portion of the 99 g. freeze-dried solids obtained by the Dowex 1×2 purification above is taken up in 0.1 M 2,6-lutidine acetate buffer, pH 6.3. The solution, 125 ml., readjusted to pH 6.3 with acetic acid, is applied to a 7.6×142 cm. column of Dowex 50×8 in the 2,6-lutidine cycle, which had previously been equilibrated with buffer. The column is developed with 0.1 M buffer at 35 ml./min. A 3.6 l. fore-cut is collected followed by 200 fractions of 20 ml. each. Every fourth fraction 6 through 194 is assayed at a dilution of 1:200. The bio-activity is contained in fractions 18 through 178, reaching a maximum in fractions 62 through 82. Fractions 42 through 102 are combined and 640 ml. of deionized water added to give 1920 ml. The pooled, diluted, solution containing 63% of the bio-activity applied on the Dowex 50×8 column, is freeze-dried.

The freeze-dried solids are dissolved in 0.1 M 2,6-lutidine acetate, pH 7.0 buffer. The solution, 25 ml., is applied to a 5×112 cm. column of Bio-Gel P-2 (200–400 mesh), which had previously been equilibrated with 0.1 M buffer. The gel is then developed with the same buffer at 10 ml./min.

The effluent stream is monitored with a Meccomatic recording differential refractometer. The development is continued until 125 fractions, 20 ml. each, are collected. Every fraction, 70 through 89, is assayed at a dilution of 1:300. The bio-activity is found in fractions 72 through 81, reaching a maximum in fraction 77. Fractions 75 through 79 are freeze-dried to obtain 100.5 mg. of antibiotic with a potency of 8,320 units/mg.

The 100.5 mg. of freeze-dried solid is taken up into 4 ml. of 0.01 M potassium phosphate buffer, pH 7. This solution, containing 692 hydroxylamine-extinguishable optical units is applied on a 1.7 cm. diameter column packed with 90 ml. prewashed XAD-2 and equilibrated prior to use with 180 ml. of 0.01 M potassium phosphate buffer, pH 7, at 5° C. The XAD-2 is washed prior to use successively with (1) 5 volumes of 1 N NaOH followed by deionized H$_2$O until effluent is neutral; (2) 5 volumes 1 N HCl followed by deionized H$_2$O until the effluent is neutral; (3) 5 volumes each of methanol, acetone, 0.001 M EDTA tetrasodium, and finally distilled H$_2$O. Vacuum is applied to all solvents before use.

After the sample is applied on the column it is followed by two, 2 ml. portions of the phosphate buffer. The column is developed at 5° C. with the buffer at a flow rate of 2 ml./min. Four ml. fractions of eluate are collected. Fractions obtained after 109 ml. of eluate has been collected and ending with the 309th ml. are combined. To this combined eluate is added the 11.53 mg. sample of XAD-2 purified antibiotic obtained above comprising 186 hydroxylamine-extinguishable optical density units. The combined eluate together with the added antibiotic is concentrated in vacuo on a rotary evaporator at a temperature below 10° C. to a volume of 7 ml.

This solution, containing 720 hydroxylamine-extinguishable optical density units is applied on a 1.7 cm. diameter column packed with 90 ml. XAD-2 prewashed as above and equilibrated at 5° C. prior to use with distilled water. The sample is followed by two, 2 ml. portions of distilled water. The column is developed with distilled water at the rate of 2 ml./min. Four ml. fractions of eluate are collected. Fractions obtained after 109 ml. of eluate have been collected and ending with the 301st ml. are pooled and concentrated on a rotary evaporator to a volume of 10.3 ml. This solution, containing 589 hydroxylamine-extinguishable optical density units, is lyophilized to yield 23.6 mg. of antibiotic with a calculated potency of 30,140 units/mg.

The antibiotic thienamycin thus prepared is a white, amorphous solid with a fibrous consistency, a sample of which on exposure in a glass capillary tube to temperatures elevated at a rate of 3° C. per minute, underwent decomposition without the intervention of a liquid phase in the following stages: softening occurred at 130° to 140° C. with a contraction in volume of the solid continuing until 170° to 174° C., in which range the material yellowed; sintering and a progressive intensification of color to reddish-brown being observed in the range 180° to 200° C. and finally carbonization and residual traces of solid being found at 205° C.

A further sample of this material on spectro-photometric analysis shows an absorbance peak at 296.5 nm with an $E_{1\ cm.}^{1\%} = 268.2$. Elemental analysis yields the following results: (1) a 5.67% weight loss upon drying at room temperature for 4 hours under vacuum, and (2) the composition 47.68% carbon, 6.22% hydrogen, 11.48% nitrogen. These results are consistent with the empirical formula $C_{11}H_{16}N_2O_4S \cdot (NH_3)_{0.28}$, the calculated elemental composition corresponding to this empirical formula being C=47.68%; H=6.13%, N=11.52%, S=11.57% and O=23.1%. Polarimetric analysis of a 1 mg./ml. solution of this sample in 10 mM potassium phosphate buffer showed a specific optical rotation $[\alpha]_D^{27°\ C.} + 80$. The infrared spectrum of a nujol mull of this sample revealed characteristic absorption peaks at 1765 cm.$^{-1}$, 1650-1550 cm.$^{-1}$, 2800-2500 cm.$^{-1}$, and 3500-3100 cm.$^{-1}$. An NMR spectrum at 100 MHz of a sample of this product dissolved in D$_2$O reveals a doublet at $\delta$ 1.275, a pair of doublets at $\delta$ 3.39 and multiplets at $\delta$ 3.15 and $\delta$ 4.20, these peaks being characteristic of thienamycin.

EXAMPLE 6

Acetylation of Thienamycin

Thienamycin, 10.9 mg. is stirred for 10 minutes at 0° C. in 1 ml. dry DMF plus 2 ml. freshly prepared acetic anhydride. The DMF and acetic anhydride are removed by washing repeatedly (5 to 6 times) with 25-40 ml. portion of hexane and one last portion of hexane after the addition of 1 ml. dry ethyl ether. The crude sample of N-actyl thienamycin is dissolved in 20 ml. of deionized water which contains 100 $\mu$moles of Tris base [tris(hydroxymethyl)aminomethane] and 35 $\mu$moles of HCl. The pH, after dissolution of the sample, is 7.9. The solution contains 244 absorbance units at 298 nm and a ¼ inch assay disc containing 0.1 ml. of a 1000 fold dilution, produces a 23 mm. zone of inhibition when incubated on ATCC 8461 plates at 25° C.

This sample is applied on a column (1.3 cm. × 14 cm. bed dimensions) of Dowex-1×4 (Cl$^-$) minus 400 mesh. The column is washed with 10 ml. of deionized water and the antibiotic, N-acetyl thienamycin, is eluted with 0.07 M NaCl + 0.005 M NH$_4$Cl + 0.0001 M NH$_3$ in deionized water. Fractions of 6.1 ml. are collected at a flow rate of 0.7 ml. per minute. The main peak of UV absorbance at 298 nm appears in fractions 36 through 50, with a maximum at fraction 40. Fractions 38 through 46 are combined, containing a total of 107 absorbance units at 298 nm. The combined fractions are rotary evaporated under reduced pressure to 2 ml. and 5 $\mu$l of 1 M NaOH is added.

This concentrate is applied on a column (2.2×80 cm. bed dimensions) of Bio-Gel P-2, 200–400 mesh. The sample is washed with two, 1 ml. portions of deionized water and eluted with deionized water at a flow rate of 0.6 ml. per minute. Fractions of 3.04 ml. are collected.

The main peak of UV absorbance at 300 nm appears in fractions 58 through 64, with a maximum at fraction 60. Fractions 59 through 62 containing 83.7 A$_{300}$ units are pooled. A portion equivalent to 2.2 A$_{300}$ units is removed for reference, and the remainder is concentrated to 1.5 ml. and lyophilized in a 14 ml. glass vial to give 3.9 mg. of N-acetyl thienamycin.

$\lambda_{max}$ 301 nm, $E_{max}/E_{min} = 4.45$, E%$_{301}$ in deionized water = 208.

EXAMPLE 7

Acetylation of Thienamycin

Step A.

Nine mg. thienamycin are stirred for 10 minutes at 0° C. in 1 ml. dry DMF plus 2 ml. freshly prepared acetic anhydride. The DMF and acetic anhydride are removed by washing repeatedly (5 to 6 times) with 25-40 ml. portions of hexane and one last portion of hexane after the addition of 1 ml. dry ethyl ether. Ten ml. cold distilled water containing 50 $\mu$l 1 M Tris-base, and 50 $\mu$l 1 M Tris.HCl, pH 8, are added. The pH of this solution is 7.8 and it contains a total of 102 hydroxylamine-extinguishable O.D. units. Ten ml. cold distilled water are added and the solution held at 0° C.

A 1.7 cm. diameter column packed with 30 ml. Dowex 1×4 Cl$^-$ (minus 400 mesh) resin is prepared and washed with 90 ml. of each of the following: (1) 0.2 M HCl, (2) 0.5 N NaCl solution containing 0.01 M HCl, (3) deionized water.

The 20 ml. sample is applied to the Dowex 1×4 column, followed by two, 2 ml. portions of deionized water and then two, 1 ml. portions of eluting buffer. The column is eluted with 0.07 M NaCl containing 0.005 M $NH_4Cl$ and 0.1 mM $NH_4OH$. The rate is 4.3 ml./5 minutes, and 4.3 ml. fractions are collected. Fractions from 555 ml. to 594 ml. are combined and stored at 5° C.

Step B.

Thienamycin 27 mg. is stirred for 10 minutes at 0° C. in 2 ml. dry DMF plus 4 ml. freshly prepared acetic anhydride. The DMF and acetic anhydride are removed by washing 6 times with 25–40 ml. portions of hexane and one last portion of hexane after addition of 2 ml. dry ethyl ether. Ten ml. cold distilled water containing 50 μl 1 M Tris-base, and 50 μl 1 M Tris.HCl, pH 8, are added and the resulting pH is 6.85. The solution contains 148 hydroxylamine-extinguishable O.D. units.

The top cm. of the Dowex 1×4 (minus 400 mesh column) described in Step A is removed and the column washed with 90 ml. of each of the following: (1) 0.2 M HCl, (2) 0.5 N NaCl solution containing 0.01 M HCl, (3) deionized water.

The 10 ml. mixture is added to 10 ml. 0° C. distilled water and is applied to the Dowex 1×4 Cl⁻ column and is followed by two, 2 ml. portions of deionized water and then two, 2 ml. portions of eluting buffer. The column is eluted with a 0.07 M NaCl solution containing 0.005 M $NH_4Cl$ and 0.1 mM $NH_4OH$. The rate is 4.3 ml./5 minutes, and 4.3 ml. fractions are collected. Fractions from 497 to 571 ml. are pooled and added to the pooled fractions from the Dowex 1×4 column described in Step A. Together these fractions contain 117.5 hydroxylamine-extinguishable O.D. units.

A 2.2 cm×62 cm. column packed with 225 ml. Bio-Gel P-2 (200–400 mesh) resin with an exclusion limit of 2600 Daltons (defined prior to use by decantation from distilled water), is prepared and washed with 50 ml. 1 M NaCl, followed by 225 ml. deionized $H_2O$. The combined Dowex 1×4 eluate pools are concentrated under vacuum to 2.66 ml. and applied to the Bio-Gel P-2 column, followed by two, 2 ml. portions of deionized water. The column is developed with deionized water at the rate of 1 ml./minute, and 2 ml. fractions are collected. Fractions from 190 ml. to 204 ml. are combined and concentrated to 2.5 ml.

A 2.2 cm.×62 cm. column packed with 225 ml. Bio-Gel P-2, 200–400 mesh resin with an exclusion limit of 1800 Daltons (defined prior to use by decantation from distilled water) is washed prior to use with 225 ml. 1 M NaCl followed by 100 ml. deionized water.

The above 2.5 ml. concentrate, containing 109.5 hydroxylamine-extinguishable O.D. units is applied to the column followed by two, 2 ml. portions of deionized water. The column is developed with deionized water at the rate of 1 ml./minute and 2 ml. fractions are collected. Fractions from 104 ml. to 132 ml. are combined and contain 97 hydroxylamine-extinguishable O.D. units. A 2.4 ml. portion is stored at 0° C. for in vitro assays and the remainder is lyophilized to give N-acetyl thienamycin.

Compositions containing the antibiotic, N-acetyl thienamycin may be administered in several unit dosage forms as, for example, in solid or liquid orally ingestible dosage form. The compositions per unit dosage, whether liquid or solid may contain from 0.1% to 99% of active material, the preferred range being from about 10 to 60%. The composition will generally contain from about 25 mg. to about 1000 mg. by weight of the active ingredient based upon the total weight of the composition; however, in general, it is preferable to employ a dosage amount in the range of from about 250 mg. to 1000 mg. or preferably in the range of about 400 to 800 mg. In parenteral administration the unit dosage is usually the pure compound in a slightly acidified sterile water solution or in the form of a soluble powder intended for solution. Representative formulations can be prepared by the following procedures:

| Capsules | Per Capsule |
|---|---|
| N-Acetyl thienamycin | 400 mg. |
| Lactose, U.S.P., a sufficient quantity to fill No. 0 Capsules, approx. 475 mg. each | |

In the above example the active compound and the diluent are mixed to produce a uniform blend, which is then filled into No. 0 hard gelatin capsules, by hand or on a suitable machine, as required. The mixing and filling is preferably done in an area having a relative humidity less than 40%.

| Tablets | Per Tablet |
|---|---|
| N-Acetyl thienamycin | 300. mg. |
| Calcium phosphate | 192. mg. |
| Lactose, U.S.P. | 190. mg. |
| Cornstarch | 80. mg. |
| Magnesium stearate | 8. mg. |
| | 800. mg. |

In the above example, the active component is blended with the calcium phosphate, lactose and about half of the cornstarch. The mixture is granulated with a 15% cornstarch paste and rough-screened and screened again through No 16 screens. The balance of the cornstarch and the magnesium stearate is added and the mixture is compressed into tablets, approximately ⅜" in diameter, each weighing 800 mg.

Alternatively, the active component is blended with the calcium phosphate, lactose and one-half the cornstarch. The mixture is "slugged" on a heavy duty press to produce compacted tablet-like masses. These are broken down to a No. 16 mesh granule. The balance of the cornstarch and the magnesium stearate are added and the mixture is compressed into tablets approximately ⅜ in diameter, each weighing 800 mg.

| Lyo Form (For Injection) | Per Vial |
|---|---|
| N-Acetyl thienamycin | 25 mg. |
| Water-for-Injection, U.S.P. to make | 5 ml. |

In the above example the active component is dissolved in sufficient water-for-injection in the ratio shown. The solution is filtered through Selas candles or Millipore membrane filters to sterilize. The solution is subdivided into sterile vials. The vials and contents are frozen, and the water is aseptically removed by lyophilization. The vials containing the sterile dry solid are aseptically sealed.

To restore for parenteral administration, 5 ml. of sterile water-for-injection is added to the contents of a vial.

| Oral Liquid Forms | Per 1000 ml. |
| --- | --- |
| N-Acetyl thienamycin | 1.0 gm. |
| Sucrose | 600.0 gm. |
| Glucose | 250.0 gm. |
| Sodium Benzoate | 1.0 gm. |
| Concentrated Orange Oil | 0.2 ml. |
| Purified water U.S.P. to make | 1000.0 ml. |

The sucrose and glucose are dissolved in about 400 ml. of water using heat to aid solution. This solution is cooled and sodium benzoate, followed by the concentrated orange oil added. The solution is brought to about 900 ml. volume with water and the antibiotic is added. The solution is clarified by filtration through a coarse filter.

What is claimed is:

1. N-Acetyl thienamycin and pharmaceutically acceptable salts thereof; said N-acetyl thienamycin exhibiting a 100 MHz nmr spectrum characterized by the following peaks: $\delta$ 1.27, d, 3H, J$\approx$6.5; $\delta$ 1.98, S, 3H; $\delta$ 2.94 m, 2H; $\delta$ 3.17, m, 2H; $\delta$ 3.38, t, 2H, J$\approx$6.5; $\delta$ 3.38, m, 1H; $\delta$ 4.20, m, 2H.

2. An antibiotic composition comprising an effective amount of a compound according to claim 1 and a non-toxic pharmaceutically acceptable carrier therefor.

* * * * *